(12) United States Patent
Vanhoudt et al.

(10) Patent No.: US 9,116,099 B2
(45) Date of Patent: Aug. 25, 2015

(54) WIDE DYNAMIC RANGE CONDUCTIVITY MEASUREMENTS IN WATER

(71) Applicant: General Electric Company, Schenectady, NY (US)

(72) Inventors: Paulus J. Vanhoudt, Broomfield, CO (US); Paul P. Kosenka, Boulder, CO (US); Krzysztof Franaszczuk, Boulder, CO (US)

(73) Assignee: General Electric Company, Schenectady, NY (US)

( * ) Notice: Subject to any disclaimer, the term of this patent is extended or adjusted under 35 U.S.C. 154(b) by 314 days.

(21) Appl. No.: 13/728,497

(22) Filed: Dec. 27, 2012

(65) Prior Publication Data

US 2014/0184251 A1 Jul. 3, 2014

(51) Int. Cl.
*G01N 27/00* (2006.01)
*G01N 27/08* (2006.01)
*G01N 27/06* (2006.01)

(52) U.S. Cl.
CPC ............... *G01N 27/08* (2013.01); *G01N 27/06* (2013.01)

(58) Field of Classification Search
CPC .................................................... G01N 27/08
USPC ........................................................ 324/722
See application file for complete search history.

(56) References Cited

U.S. PATENT DOCUMENTS

| 3,604,016 | A | | 9/1971 | Robinson et al. |
| 3,661,748 | A | | 5/1972 | Blackmer |
| 3,772,591 | A | | 11/1973 | Louder et al. |
| 3,816,671 | A | | 6/1974 | Fraim et al. |
| 4,132,944 | A | | 1/1979 | Bentz |
| 4,190,827 | A | | 2/1980 | Diamond |
| 4,469,760 | A | | 9/1984 | Giner et al. |
| 4,482,967 | A | | 11/1984 | Evans, Jr. et al. |
| 4,656,427 | A | | 4/1987 | Dauphinee |
| 4,751,189 | A | | 6/1988 | Rocklin |
| 4,786,875 | A | | 11/1988 | Carll |
| 4,806,912 | A | | 2/1989 | Clack |
| 4,851,818 | A | | 7/1989 | Brown et al. |
| 5,221,448 | A | | 6/1993 | Weinberger et al. |
| 5,260,663 | A | * | 11/1993 | Blades .......................... 324/442 |

(Continued)

FOREIGN PATENT DOCUMENTS

WO 2007107108 A1 9/2007

OTHER PUBLICATIONS

Amersham Biosciences, "Monitor pH/C-900 Data File" (1998).

(Continued)

*Primary Examiner* — Jeff Natalini
(74) *Attorney, Agent, or Firm* — Wegman, Hessler & Vanderburg

(57) ABSTRACT

A conductivity meter for measuring the conductivity of a fluid is provided. The conductivity meter has a cell circuit and a control unit circuit. The cell circuit has a square wave drive amp, a cell, and a trans-impedance amplifier. The fluid flows through the cell. The control unit circuit and the square wave drive amp are configured to apply a square wave pulse train having a voltage to the fluid of the cell, thereby inducing a flow of current through the fluid in the cell. The cell circuit trans-impedance amplifier and the control unit circuit are configured to obtain a plurality of measurements of current flowing through the fluid in the cell and estimate a raw conductivity of the fluid in the cell using the current flow measurements. A method for measuring the conductivity of a fluid is also provided.

20 Claims, 14 Drawing Sheets

(56) References Cited

U.S. PATENT DOCUMENTS

| | | | |
|---|---|---|---|
| 5,317,275 | A | 5/1994 | Mount et al. |
| 5,334,940 | A | 8/1994 | Blades |
| 5,384,461 | A | 1/1995 | Jullien et al. |
| 5,677,190 | A | 10/1997 | Melanson et al. |
| 5,708,363 | A | 1/1998 | Yates et al. |
| 6,529,841 | B2 * | 3/2003 | Cocking et al. ............... 702/65 |
| 6,842,017 | B2 * | 1/2005 | McKenzie et al. ............ 324/663 |
| 7,442,297 | B2 | 10/2008 | Larkner et al. |
| 7,550,979 | B2 * | 6/2009 | Zhou et al. ................... 324/693 |
| 7,799,194 | B2 | 9/2010 | Makuska |
| 8,022,355 | B2 | 9/2011 | Kulik et al. |
| 8,038,868 | B2 | 10/2011 | Hirshberg et al. |
| 8,084,749 | B2 | 12/2011 | Griep-Raming et al. |
| 8,172,999 | B2 | 5/2012 | Wen et al. |
| 8,840,767 | B2 | 9/2014 | Wen et al. |
| 2002/0040121 | A1 | 4/2002 | Hsia |
| 2003/0040122 | A1 | 2/2003 | Blades et al. |
| 2010/0084276 | A1 * | 4/2010 | Lindsay .......................... 205/93 |
| 2010/0188111 | A1 | 7/2010 | Fougere |
| 2013/0322200 | A1 | 12/2013 | Ludwig |

OTHER PUBLICATIONS

Bevilacqua, "Ultrapure Water—The Standard for Resistivity Measurements of Ultrapure Water" Semiconductor Pure Water and Chemicals Conference (1998).

International Search Report and Written Opinion issued in connection with corresponding PCT Application No. PCT/US2013/075542 on Mar. 12, 2014.

Lee et al., "An on-line instrument for measuring small quantities of dispersed non-conducting liquid in a conducting liquid", Measurement and Control, vol. No. 7, Issue No. 9, pp. 341-345, Sep. 1, 1974.

Czaja, "A microcontroller system for measurement of three independent components in impedance sensors using a single square pulse", Sensors and Actuators A: Physical, vol. No. 173, Issue No. 1, pp. 284-292, Oct. 17, 2011.

* cited by examiner

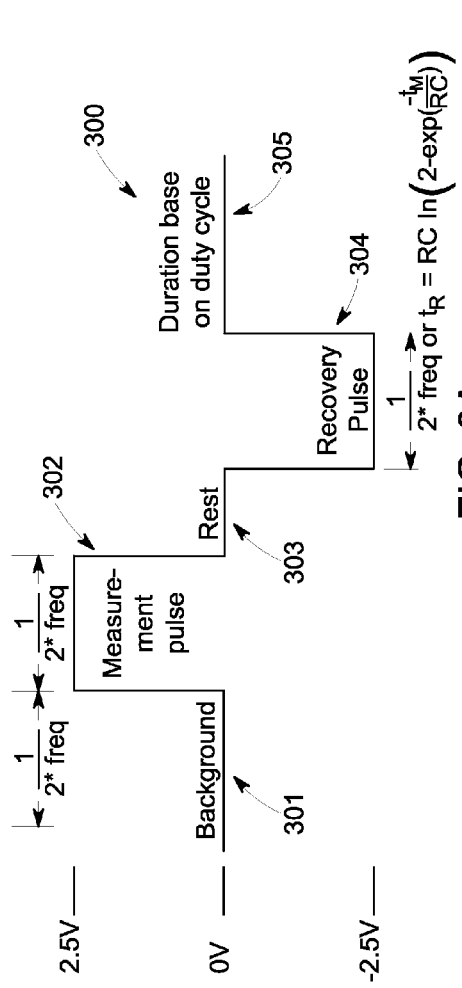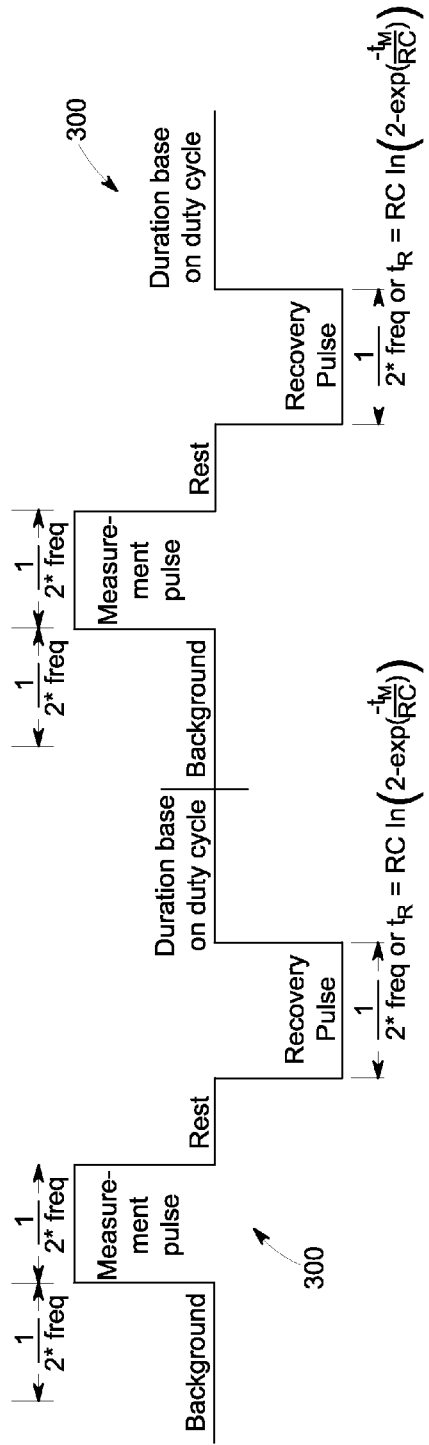
FIG. 3A
FIG. 3B

Theoretical conductivity of pure water

| T°C | Conductivity of $H_2O$ (nS/cm) |
|---|---|
| 0 | 11.6 |
| 5 | 16.53 |
| 10 | 230.3 |
| 15 | 31.38 |
| 20 | 41.93 |
| 25 | 55.01 |
| 30 | 70.97 |
| 35 | 90.17 |
| 40 | 113 |
| 45 | 139.8 |
| 50 | 170.9 |
| 55 | 206.6 |
| 60 | 247.4 |
| 65 | 293.5 |
| 70 | 345.3 |
| 75 | 402.9 |
| 80 | 466.9 |
| 85 | 537.1 |
| 90 | 613.5 |
| 95 | 696.4 |
| 100 | 784.9 |

FIG. 5

The equivalent conductance of the separate ions
(Conductance in nanosiemens per centimeter per milliequivalent per liter)

| Ion | 0°C | 18°C | 25°C | 50°C | 75°C | 100°C | 128°C | 156°C |
|---|---|---|---|---|---|---|---|---|
| K | 40400 | 64600 | 74500 | 115000 | 159000 | 206000 | 263000 | 317000 |
| Na | 26000 | 43500 | 50900 | 82000 | 116000 | 155000 | 203000 | 249000 |
| $NH_4$ | 40200 | 64500 | 74500 | 115000 | 159000 | 207000 | 264000 | 319000 |
| Ag | 32900 | 54300 | 63500 | 101000 | 143000 | 188000 | 245000 | 299000 |
| ½Ba | 33000 | 55000 | 65000 | 104000 | 149000 | 200000 | 262000 | 322000 |
| ½Ca | 30000 | 51000 | 60000 | 98000 | 142000 | 191000 | 252000 | 312000 |
| ½La | 35000 | 61000 | 72000 | 119000 | 173000 | 235000 | 312000 | 388000 |
| Cl | 41100 | 65500 | 75500 | 116000 | 160000 | 207000 | 264000 | 318000 |
| $NO_2$ | 40400 | 61700 | 70600 | 104000 | 140000 | 178000 | 222000 | 263000 |
| $C_2H_2O_2$ | 20300 | 34600 | 40800 | 67000 | 96000 | 130000 | 171000 | 211000 |
| ½$SO_4$ | 41000 | 68000 | 79000 | 125000 | 177000 | 234000 | 303000 | 370000 |
| ½$C_2O_4$ | 39000 | 63000 | 73000 | 115000 | 163000 | 213000 | 275000 | 336000 |
| ½$C_5H_6O_7$ | 36000 | 60000 | 70000 | 113000 | 161000 | 214000 | | |
| ½$Fe(CN)_6$ | 58000 | 95000 | 111000 | 173000 | 244000 | 321000 | | |
| H | 240000 | 314000 | 350000 | 465000 | 565000 | 644000 | 722000 | 777000 |
| OH | 105000 | 172000 | 192000 | 284000 | 360000 | 439000 | 525000 | 592000 |

FIG. 6

WIDE DYNAMIC RANGE CONDUCTIVITY MEASUREMENTS IN WATER

FIELD OF THE INVENTION

This present invention is directed to electronic circuits and a method of using said circuits for sensing the conductivity of a fluid.

BACKGROUND OF THE INVENTION

Some industrial systems require a liquid having a specific conductivity to be used, such as pure water. Therefore, it is important to monitor the conductivity of the liquid in such systems. In the past, some conductivity meters made measured conductivity over an extended range by dividing up the range into several decades and providing a separate conductivity cell for each decade. However, a conductivity meter that contains multiple conductivity cells is bulky and impractical for industrial applications. Further, the separate conductivity cells were only calibrated for one fixed frequency, usually the frequency located in the middle of the decade. However, because of non-linear effects, the measurements associated with values lying at the edges of each decade were not as accurate.

Accordingly, there is a need for a conductivity meter that accurately measures conductivity over a range of several decades, eliminates the need for multiple conductivity cells, and minimizes the non-linear effects detrimental to accuracy. The present invention satisfies this need.

Further, there is a need for a meter that can be calibrated to a standard (NIST) on the outskirt of the meter's conductivity range and maintain accuracy throughout the meter's entire conductivity range. The present invention satisfies this need.

BRIEF SUMMARY OF THE INVENTION

In one aspect of the invention, a conductivity meter for measuring the conductivity of a fluid comprising: a cell circuit and a control unit circuit; the cell circuit comprising a square wave drive amp, a cell, and a trans-impedance amplifier; wherein the fluid flows through the cell; wherein the control unit circuit and the square wave drive amp are configured to apply a square wave pulse train having a voltage to the fluid of the cell, thereby inducing a flow of current through the fluid in the cell; wherein the cell circuit trans-impedance amplifier and the control unit circuit are configured to obtain a plurality of measurements of current flowing through the fluid in the cell and estimate a raw conductivity of the fluid in the cell using the current flow measurements.

In another aspect of the invention, the square wave pulse train is comprised of a background stage, a measurement pulse, a recovery pulse, and a base stage.

In another aspect of the invention, the square wave pulse train is further comprised of a rest stage.

In another aspect of the invention, the measurement pulse has a duration which is determined by a previous raw conductivity value.

In another aspect of the invention, the measurement pulse has a duration of 1/(2*drive frequency), wherein the drive frequency is determined by a previous raw conductivity value.

In another aspect of the invention, the current flow measurements are values for the net current flowing through the fluid in said cell.

In another aspect of the invention, the control unit circuit estimates the raw conductivity value of the fluid in the cell by fitting the current flow measurements to a double exponent decay function.

In another aspect of the invention, the conductivity meter further comprises a thermistor circuit, wherein the thermistor circuit and the control unit circuit are configured to calculate the temperature of the fluid in the cell and apply a temperature correction to the raw conductivity value of the fluid, thereby producing a temperature corrected conductivity value.

In another aspect of the invention, the thermistor circuit is comprised of a thermistor switch, thermistor drive, thermistor, and trans-impedance amplifier.

In another aspect of the invention, the cell circuit trans-impedance amplifier has a feedback resistor value which is determined by a position of a gain control circuit; wherein the position of the gain control circuit is determined by a previous raw conductivity value.

In another aspect of the invention, the cell circuit is further comprised of a polarity switching circuit, wherein the polarity switching circuit is configured to pass voltage to the square wave drive amp and dictate the polarity of the voltage applied to the cell by the square wave drive amp.

In another aspect of the invention, the polarity switching circuit is further comprised of a cell switch and a polarity switch.

In another aspect of the invention, the cell circuit is further comprised of a rectifier configured to rectify the output of the trans-impedance amplifier.

In yet another aspect of the invention, A method for measuring the conductivity of a fluid comprising: providing a cell circuit having a cell containing a fluid having a conductivity; applying a square wave pulse train to the cell, thereby causing a current to flow through the fluid in the cell; obtaining a plurality of measurements of current flowing through the fluid in the cell; and estimating a raw conductivity value of the fluid by fitting an equation through the current flow measurements, wherein the equation contains the term 1/R, where R equals the resistance of the fluid in the cell.

In another aspect of the invention, the current flow measurements are values for the net current flowing through the fluid in the cell.

In another aspect of the invention, the equation is a double exponent decay function.

In another aspect of the invention, the square wave pulse train is comprised of a measurement pulse during which the current flow measurements are taken.

In another aspect of the invention, the square wave pulse train is further comprised of a background stage, recovery pulse, and a base stage.

In another aspect of the invention, the square wave pulse train is further comprised of a rest stage.

In another aspect of the invention, the method further comprises measuring the temperature of the fluid in the cell and applying a temperature correction to the raw conductivity value of the fluid, thereby producing a temperature corrected conductivity value.

Advantages of the present invention will become more apparent to those skilled in the art from the following description of the embodiments of the invention which have been shown and described by way of illustration. As will be realized, the invention is capable of other and different embodiments, and its details are capable of modification in various respects.

BRIEF DESCRIPTION OF SEVERAL VIEWS OF THE DRAWINGS

These and other features of the present invention, and their advantages, are illustrated specifically in embodiments of the invention now to be described, by way of example, with reference to the accompanying diagrammatic drawings, in which:

FIG. 3A illustrates one period of a square wave pulse train in accordance with an embodiment of the present invention;

FIG. 3B illustrates multiple periods of a square wave pulse train in accordance with an embodiment of the present invention;

FIG. 5 is a table of the theoretical conductivity of pure water;

FIG. 6 is a table of the equivalent conductance of the separate ions; and

Figure 1A:
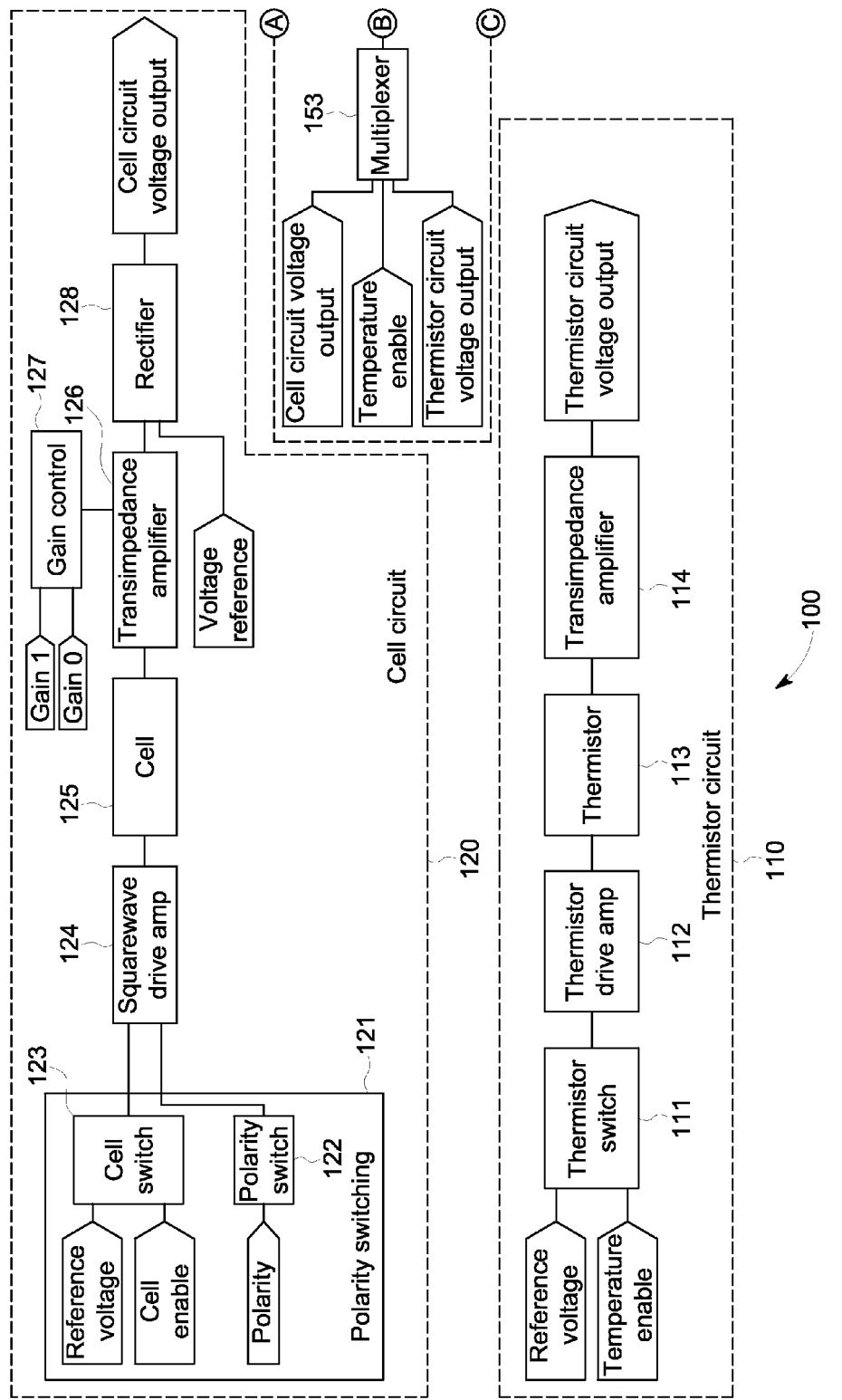
FIGS. 1A-C illustrates a block diagram of a conductivity meter according to an embodiment of the present invention.

It should be noted that all the drawings are diagrammatic and not drawn to scale. Relative dimensions and proportions of parts of these figures have been shown exaggerated or reduced in size for the sake of clarity and convenience in the drawings. The same reference numbers are generally used to refer to corresponding or similar features in the different embodiments. Accordingly, the drawing(s) and description are to be regarded as illustrative in nature and not as restrictive.

DETAILED DESCRIPTION OF THE PREFERRED EMBODIMENT

Figure 1B:
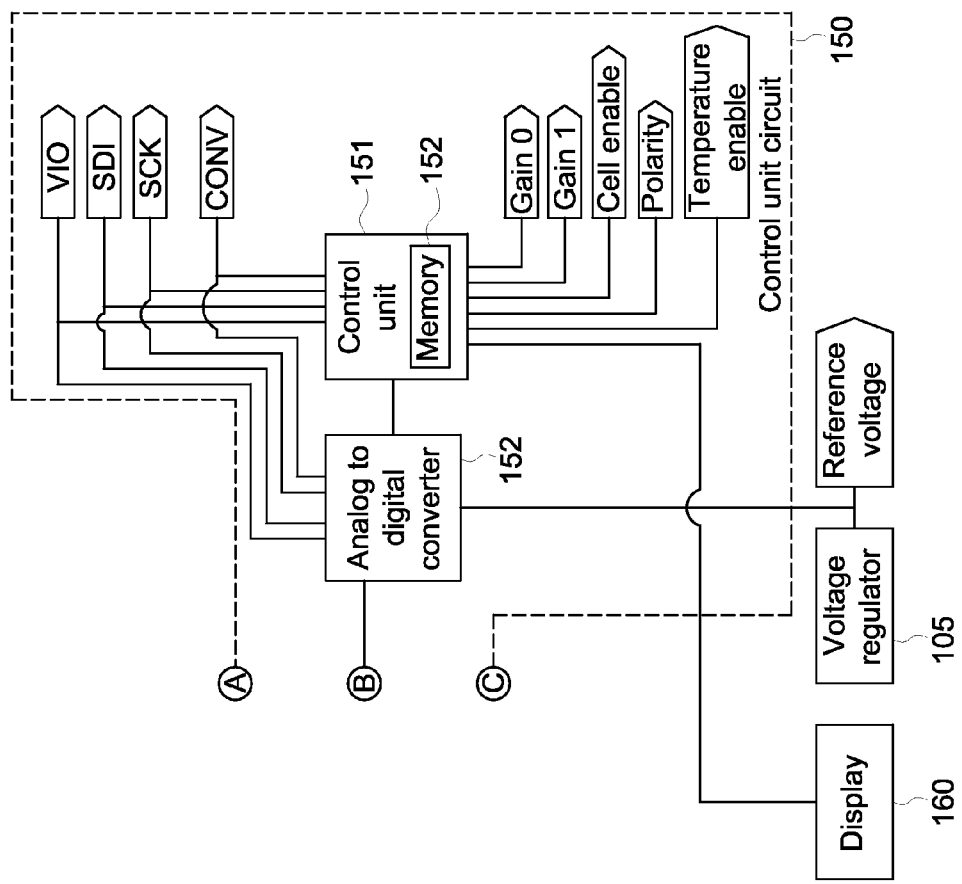
Figure 1C:
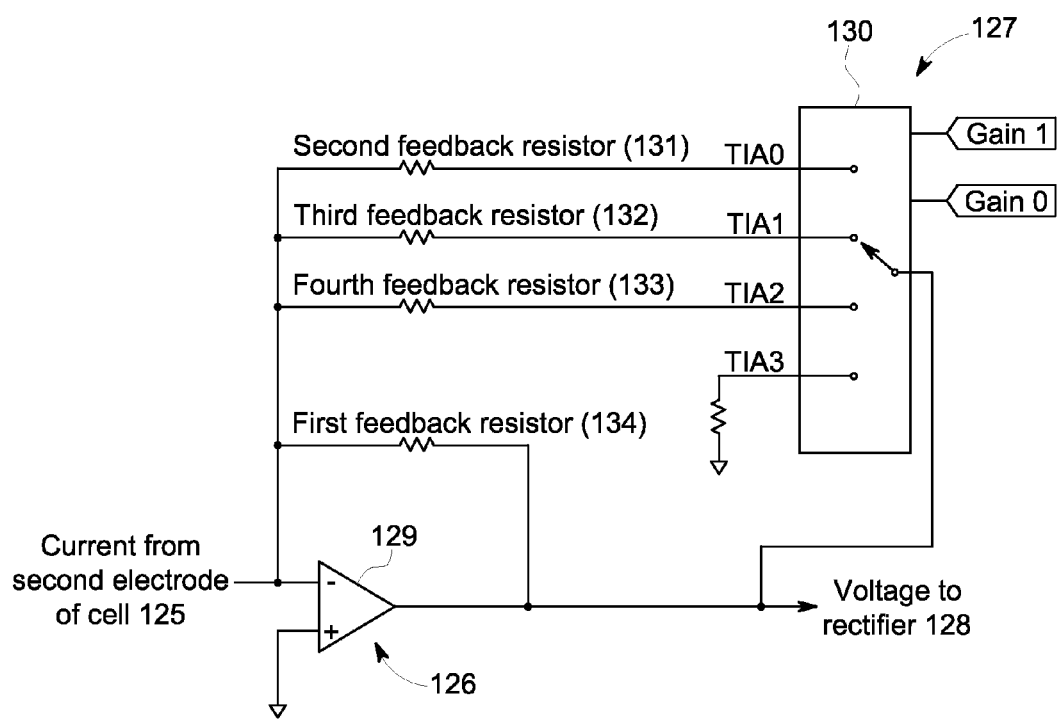

Referring now to the FIGS. 1A-C, there is shown a circuit for conductivity meter 100 for measuring conductivity and temperature of a target fluid. Referring to the block diagram of an embodiment of conductivity meter 100 in FIG. 1, conductivity meter 100 is comprised of a voltage regulator 105, cell circuit 120, control unit circuit 150, display 160, and thermistor circuit 110. Cell circuit 120 is comprised of polarity switching circuit 121, squarewave drive amplifier 124, cell 125, trans-impedance amplifier 126, gain control circuit 127, and rectifier 128. Thermistor circuit 110 is comprised of thermistor switch 111, thermistor drive 112, thermistor 113, and trans-impedance amplifier 114. Control unit circuit 150 is comprised of multiplexer 153, analog-to-digital converter 152, and control unit 151. Control unit 151 has memory 152.

Voltage regulator 105 provides a reference voltage to analog-to-digital converter 152, cell switch 123, rectifier 128, and thermistor switch 111. The rectifier 128 helps to ensure that the voltages arriving at analog-to-digital converter 152 are not negative.

In one embodiment of thermistor circuit 110, thermistor switch 111 receives a TEMPERATURE ENABLE signal from control unit 151, which enables control unit 151 to control the output of thermistor drive 112. When thermistor switch 111 receives a high TEMPERATURE ENABLE signal from control unit 151, thermistor switch 111 passes the reference voltage from voltage regulator 105 to thermistor drive 112, which applies a precision voltage to thermistor 113 located in cell 125. The resistance of the thermistor 113 varies significantly with the temperature of the fluid in cell 125, more so than a standard resistor. Trans-impedance amplifier 114 measures the amount of current flowing through thermistor 113 and produces an output voltage that is representative of the amount of current flowing through thermistor 113. The output voltage of thermistor trans-impedance amplifier 114, the thermistor circuit voltage output, is directed to multiplexer 153.

In one embodiment of cell circuit 120, polarity switch 122 receives a POLARITY signal from control unit 151, and cell switch 123 receives a CELL ENABLE signal from control unit 151. Polarity switching circuit 121 works in conjunction with control unit 151 to control squarewave drive amplifier 124.

When cell switch 123 receives a high CELL ENABLE signal from control unit 151, cell switch 123 passes the reference voltage from voltage regulator 105 to squarewave drive amplifier 124, which causes squarewave drive amplifier 124 to apply a precision voltage to the fluid in cell 125 and results in an electrical current flowing through the fluid in cell 125. When polarity switch 122 receives a high POLARITY signal from control unit 151, polarity switch 122 grounds the non-inverting input of squarewave drive amplifier 124, which changes the polarity of the precision voltage applied to the fluid in cell 125. In one embodiment, cell 125 includes two metal electrodes, a first and second electrode, spaced apart from one another and configured to be exposed to the fluid in cell 125, however it is contemplated that in other embodiments, a person having ordinary skill in the art can choose to use a different suitable type of conductivity cell. Squarewave drive amplifier 124 applies voltage to the fluid in cell 125 through first electrode of cell 125.

Cell circuit trans-impedance amplifier 126 measures the amount of current flowing through the fluid in cell 125 and produces an output voltage that is representative of the amount of current flowing through the fluid in cell 125. Cell circuit trans-impedance amplifier 126 receives current from cell 125 through the second electrode. The gain of trans-impedance amplifier 126 is determined by the setting of gain control circuit switch 130 in gain control circuit 127, which is controlled by the GAIN1 and GAIN0 signals from control unit 151. The equation for the voltage output of trans-impedance amplifier 126 is $V_{TIA}=I_{CELL}R_{FEEDBACK}$, where $V_{TIA}$ is the voltage output of trans-impedance amplifier 126, $I_{CELL}$ is the amount of current flowing through cell 125, and $R_{FEEDBACK}$ is the feedback resistance value that is seen by trans-impedance amplifier 126, which is determined by gain control circuit 127.

In one embodiment, $R_{FEEDBACK}$ of trans-impedance amplifier 126 is a 4.99M resistor in parallel with the resistance value of gain control circuit 127. Gain control circuit 127 has four positions, TIA 0-3. In TIA 0, a 499Ω resistor is placed in parallel with the 4.99M resistor of trans-impedance amplifier 126, which results in a $R_{FEEDBACK}$ value of 499Ω for trans-impedance amplifier 126. In TIA 1, a 27.4 k resistor is placed in parallel with the 4.99M resistor of trans-impedance amplifier 126, which results in a $R_{FEEDBACK}$ value of 27.3 k for trans-impedance amplifier 126. In TIA 2, a 499 k resistor is placed in parallel with the 4.99M resistor of trans-impedance amplifier 126, which results in a $R_{FEEDBACK}$ value of 454 k for trans-impedance amplifier 126. In TIA 3, a resistor is not placed in parallel with the 4.99M resistor of trans-impedance amplifier 126, which results in a $R_{FEEDBACK}$ value of 4.99M for trans-impedance amplifier 126.

Control unit 151 adjusts the gain of trans-impedance amplifier 126 as necessary to prevent the output of trans-impedance amplifier 126 from riding a power rail. This is known as auto-ranging, and allows the conductivity meter to read a wider range of fluid conductivity values than if trans-impedance amplifier 126 had a non-variable feedback resistor value. The output voltage from cell trans-impedance amplifier 126 is rectified by rectifier 128. The output voltage of rectifier 128, cell circuit voltage output, is then directed to multiplexer 153.

Multiplexer 153 receives a TEMPERATURE ENABLE signal from control unit 151, which allows control unit 151 to control whether multiplexer 153 passes the cell circuit voltage output or the thermistor circuit voltage output to analog-to-digital converter 152. Multiplexer 153 directs the cell circuit voltage output and thermistor circuit voltage output to analog-to-digital converter 152, which passes the digitized values for the cell circuit voltage output and thermistor circuit voltage output to control unit 151. Analog-to-digital converter 152 receives a VIO, SDI, SCK, and CONV signal from control unit 151, which allows control unit 151 to control analog-to-digital converter 152.

It is contemplated that in other embodiments, control unit 151 can be a field programmable gate array, microprocessor, microcontroller, programmable logic controller, or another type of controller with similar functionality. Further, it is contemplated that in other embodiments, a person having ordinary skill in the art may choose to use a control unit 151 that also functions as analog-to-digital converter 152, or multiplexer 153 and analog-to-digital converter 152.

Display 160 makes information contained within control unit 151 available to the user of conductivity meter 100. In one embodiment, display 160 provides the user with a readout of the conductivity of the fluid in cell 125. In another embodiment, display 160 provides the user with a readout of the temperature and conductivity of the fluid in cell 125. It is contemplated that in other embodiments, a person having ordinary skill in the art can choose to have display 160 provide the user with any of the information contained within control unit 151. Further, in some embodiments, display 160 is a touch screen, which allows the user to interact with conductivity meter 100, such as making the selections and entering the information discussed in conjunction with step 410 below. In other embodiments, a keypad is provided, which allows the user to interact with conductivity meter 100, such as making the selections and entering the information discussed in conjunction with step 410 below.

Because of its wide conductivity range, conductivity meter 100 allows for direct calibration with NIST calibration standard of 1.46 mS/cm.

FIG. 1C shows the interaction between cell trans-impedance amplifier 126 and gain control circuit 127 in greater detail in accordance with an embodiment of the invention. As can be seen, cell trans-impedance amplifier 126 is comprised of operational amplifier 129 and first feedback resistor 134 in a trans-impedance amplifier configuration. Operational amplifier 129 receives current from second electrode of cell 125 at its inverting input, and outputs voltage to rectifier 128.

Gain control circuit 127 is comprised of gain control circuit switch 130, second feedback resistor 131, third feedback resistor 132, and fourth feedback resistor 133. Gain control circuit switch 130 has a first position (TIA 0), second position (TIA 1), third position (TIA 2), and a fourth position (TIA 3). Gain control circuit switch 130 interfaces with and is controlled by control unit 151 through the GAIN1 and GAIN0 control signals from control unit 151. In one embodiment, the resistance of first feedback resistor 134 is greater than the resistance of fourth feedback resistor 133, the resistance of fourth feedback resistor 133 is greater than the resistance of third feedback resistor 132, and the resistance of third feedback resistor 132 is greater than the resistance of second feedback resistor 131.

$R_{FEEDBACK}$ is the feedback resistance value that is seen by operational amplifier 129 of trans-impedance amplifier 126. When gain control circuit switch 130 is in the first position (TIA0) second feedback resistor 131 is placed in parallel with first feedback resistor 134. When gain control circuit switch 130 is in the second position (TIA1) third feedback resistor 132 is placed in parallel with first feedback resistor 134. When gain control circuit switch 130 is in the third position (TIA2) fourth feedback resistor 133 is placed in parallel with first feedback resistor 134. When gain control circuit switch 130 is in the fourth position (TIA3) another resistor is not placed in parallel with first feedback resistor 134. Accordingly, the value of $R_{FEEDBACK}$ seen by operational amplifier 129 in the first through fourth positions of gain control circuit switch 130 is:

| Position of Gain Control Circuit Switch (130) | Value of $R_{FEEDBACK}$ |
|---|---|
| First Position (TIA 0) | $\dfrac{1}{\dfrac{1}{\text{first feedback resistor 134}} + \dfrac{1}{\text{second feedback resistor 131}}}$ |
| Second Position (TIA 1) | $\dfrac{1}{\dfrac{1}{\text{first feedback resistor 134}} + \dfrac{1}{\text{third feedback resistor 132}}}$ |
| Third Position (TIA 2) | $\dfrac{1}{\dfrac{1}{\text{first feedback resistor 134}} + \dfrac{1}{\text{fourth feedback resistor 133}}}$ |
| Fourth Position (TIA 3) | first feedback resistor 134 |

Figure 2A:
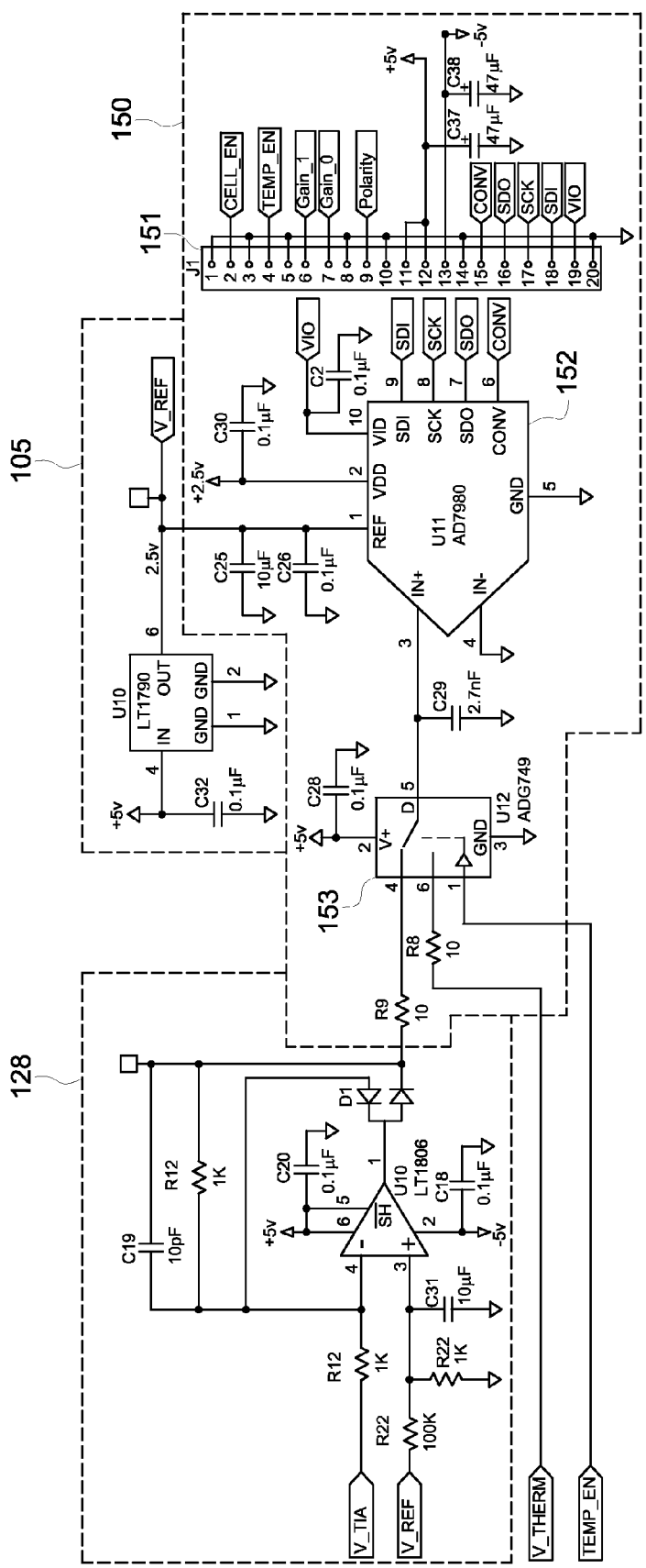
FIG. 2A-C illustrate a schematic for a conductivity meter according to an embodiment of the present invention.
Figure 2B:
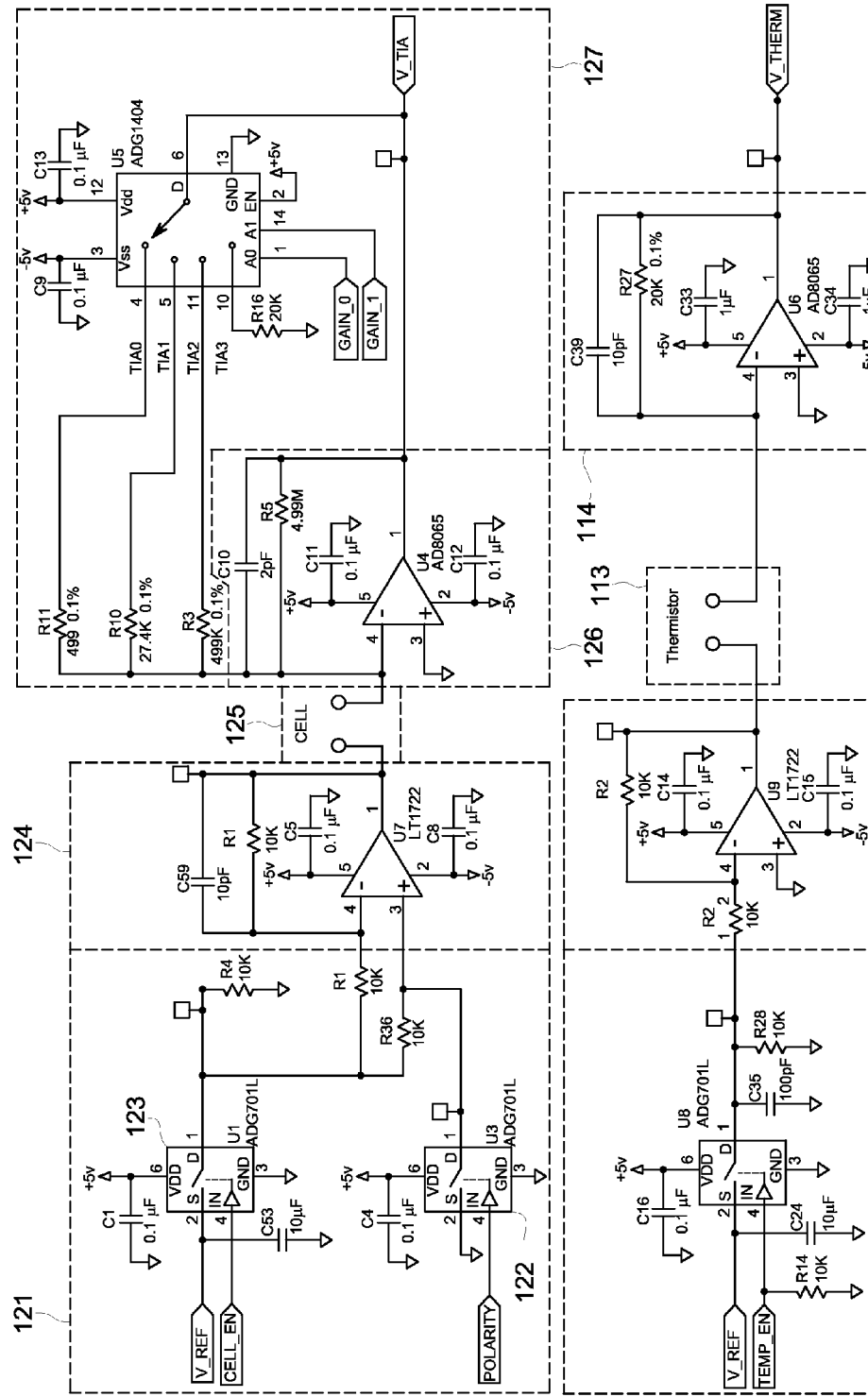
Figure 2C:
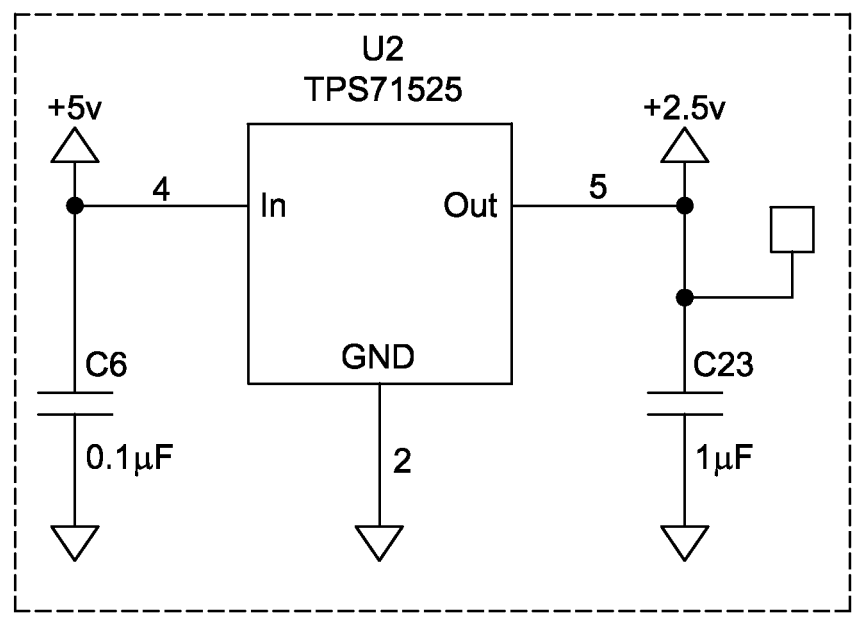

Turning now to FIGS. 2A-2C, a schematic of conductivity meter 100 is shown. Polarity switching circuit 121 of conductivity meter 100 is comprised of cell switch 123 and polarity switch 122.

Cell switch 123 is comprised of:

| REF DES | VALUE | Description | MANUFACTURER | MFG P/N |
|---|---|---|---|---|
| C1 | 0.1 uF | CAP .10 UF 16 V CERAMIC X7R 0603 | Kemet | C0603C104K4RACTU |
| C53 | 10 uF | CAP CERAMIC 10 UF 6.3 V X5R 0603 | Panasonic - ECG | ECJ-1VB0J106M |
| U1 | ADG701L | IC SWITCH SPST SOT23-6 | Analog Devices Inc | ADG701LBRTZ-REEL7 |
| R4 | 10K | RES 10.0K OHM 1/10 W 1% 0603 SMD | Vishay/Dale | CRCW060310K0FKEA |

Polarity switch 122 is comprised of:

| REF DES | VALUE | Description | MANUFACTURER | MFG P/N |
|---|---|---|---|---|
| R36 | 10K | RES 10.0K OHM 1/10 W 1% 0603 SMD | Vishay/Dale | CRCW060310K0FKEA |
| C4 | 0.1 uF | CAP .10 UF 16 V CERAMIC X7R 0603 | Kemet | C0603C104K4RACTU |
| U3 | ADG701L | IC SWITCH SPST SOT23-6 | Analog Devices Inc | ADG701LBRTZ-REEL7 |

Squarewave drive amplifier 124 is comprised of:

| REF DES | VALUE | Description | MANUFACTURER | MFG P/N |
|---|---|---|---|---|
| C59 | 10 pF | CAP CERAMIC 10 PF 50 V NP0 0603 | Kemet | C0603C100J5GACTU |
| R1 | 10K/10K | RES NET 10K/10K OHM ISO 0805 | Susumu | RM2012B-103/103-PBVW10 |
| C5 | 0.1 uF | CAP .10 UF 16 V CERAMIC X7R 0603 | Kemet | C0603C104K4RACTU |
| C8 | 0.1 uF | CAP .10 UF 16 V CERAMIC X7R 0603 | Kemet | C0603C104K4RACTU |
| U7 | LT1722 | IC OPAMP PREC 200 MHZ TSOT-23-5 | Linear Technology | LT1722CS5#TRMPBF |

Cell 125 is comprised of a conductivity cell, such as miniature conductivity cell model number ACO 08060, manufactured by GE Analytical Instruments.

Trans-impedance amplifier 126 is comprised of:

| REF DES | VALUE | Description | MANUFACTURER | MFG P/N |
|---|---|---|---|---|
| C10 | 2 pF | CAP CER 2.0 PF 50 V C0G 0603 | Murata Electronics | GRM1885C1H2R0CZ01D |
| R5 | 4.99M | RES 4.99M OHM 1/8 W 1% 0805 SMD | Vishay/Dale | CRCW08054M99FKEA |
| C11 | 0.1 uF | CAP .10 UF 16 V CERAMIC X7R 0603 | Kemet | C0603C104K4RACTU |
| U4 | AD8065 | IC OPAMP FET-IN HP HS SOT23-5 | Analog Devices Inc | AD8065ARTZ-REEL7 |
| C12 | 0.1 uF | CAP .10 UF 16 V CERAMIC X7R 0603 | Kemet | C0603C104K4RACTU |

Gain control circuit 127 is comprised of:

| REF DES | VALUE | Description | MANUFACTURER | MFG P/N |
|---|---|---|---|---|
| R11 | 499 | RES 1/10 W 499 OHM .1% 0805 | Stackpole | RNCS0805BKE499R |
| R10 | 27.4K | RES 1/10 W 27.4K OHM .1% 0805 | Stackpole | RNCS0805BKE27K4 |
| R3 | 499K | RES 1/10 W 499K OHM .1% 0805 | Stackpole | RNCS0805BKE499K |
| R16 | 20K | RES 20.0K OHM 1/10 W 1% 0603 SMD | Vishay/Dale | CRCW060320K0FKEA |
| C9 | 0.1 uF | CAP .10 UF 16 V CERAMIC X7R 0603 | Kemet | C0603C104K4RACTU |
| C13 | 0.1 uF | CAP .10 UF 16 V CERAMIC X7R 0603 | Kemet | C0603C104K4RACTU |
| U5 | ADG1404 | IC SW MUX ANALOG 4: 1 14-TSSOP | Analog Devices Inc | ADG1404YRUZ |

Rectifier 128 is comprised of:

| REF DES | VALUE | Description | MANUFACTURER | MFG P/N |
|---|---|---|---|---|
| C19 | 10 pF | CAP CERAMIC 10 PF 50 V NP0 0603 | Kemet | C0603C100J5GACTU |
| R12 | 1K/1K | RES NET 1.0K/1.0K OHM ISO 0805 | Susumu | RM2012B-102/102-PBVW10 |
| C20 | 0.1 uF | CAP .10 UF 16 V CERAMIC X7R 0603 | Kemet | C0603C104K4RACTU |
| C18 | 0.1 uF | CAP .10 UF 16 V CERAMIC X7R 0603 | Kemet | C0603C104K4RACTU |
| D1 | RB706F-40 | DIODE SCHOTTKY 40 V 30 MA SOT-323 | Rohm | RB706F-40T106 |
| C31 | 10 uF | CAP CERAMIC 10 UF 6.3 V X5R 0603 | Panasonic - ECG | ECJ-1VB0J106M |
| R22 | 1K/100K | RES NET 1.0K/100K OHM ISO 0805 | Susumu | RM2012B-102/104-PBVW10 |
| U10 | LT1806 | IC OPAMP R-R IN/OUT SGL SOT23-6 | Linear Technology | LT1806CS6#TRMPBF |

Multiplexer 153 is comprised of:

| REF DES | VALUE | Description | MANUFACTURER | MFG P/N |
|---|---|---|---|---|
| C28 | 0.1 uF | CAP .10 UF 16 V CERAMIC X7R 0603 | Kemet | C0603C104K4RACTU |
| R8 | 10 | RES 10.0 OHM 1/10 W 1% 0603 SMD | Vishay/Dale | CRCW060310R0FKEA |
| R9 | 10 | RES 10.0 OHM 1/10 W 1% 0603 SMD | Vishay/Dale | CRCW060310R0FKEA |
| U12 | ADG749 | IC SWITCH SPDT SC70-6 | Analog Devices Inc | ADG749BKSZ-REEL7 |

Voltage Regulator 105 is comprised of:

| REF DES | VALUE | Description | MANUFACTURER | MFG P/N |
|---|---|---|---|---|
| C32 | 0.1 uF | CAP .10 UF 16 V CERAMIC X7R 0603 | Kemet | C0603C104K4RACTU |
| U13 | LT1790 | IC REF LDO 2.5 V MICROPWR SOT23-6 | Linear Technology | LT1790BCS6-2.5#TRMPBF |

Analog-to-digital converter 152 is comprised of:

| REF DES | VALUE | Description | MANUFACTURER | MFG P/N |
|---|---|---|---|---|
| C25 | 10 uF | CAP CERAMIC 10 UF 6.3 V X5R 0603 | Panasonic - ECG | ECJ-1VB0J106M |
| C26 | 0.1 uF | CAP .10 UF 16 V CERAMIC X7R 0603 | Kemet | C0603C104K4RACTU |
| C30 | 0.1 uF | CAP .10 UF 16 V CERAMIC X7R 0603 | Kemet | C0603C104K4RACTU |
| C29 | 2.7 nF | CAP CER 2700 PF 50 V COG 0603 | Murata Electronics | GRM1885C1H272JA01D |
| C2 | 0.1 uF | CAP .10 UF 16 V CERAMIC X7R 0603 | Kemet | C0603C104K4RACTU |
| U11 | AD7980 | ADC 16 BIT 1MSPS 2.5LSB 10-MSOP | Analog Devices Inc | AD7980ARMZRL7 |

Thermistor switch 111 is comprised of:

| REF DES | VALUE | Description | MANUFACTURER | MFG P/N |
|---|---|---|---|---|
| C16 | 0.1 uF | CAP .10 UF 16 V CERAMIC X7R 0603 | Kemet | C0603C104K4RACTU |
| R14 | 10K | RES 10.0K OHM 1/10 W 1% 0603 SMD | Vishay/Dale | CRCW060310K0FKEA |
| C24 | 10 uF | CAP CERAMIC 10 UF 6.3 V X5R 0603 | Panasonic - ECG | ECJ-1VB0J106M |
| C35 | 100 pF | CAP CERAMIC 100 PF 50 V NP0 0603 | Kemet | C0603C101J5GACTU |
| R28 | 10K | RES 10.0K OHM 1/10 W 1% 0603 SMD | Vishay/Dale | CRCW060310K0FKEA |
| U8 | ADG701L | IC SWITCH SPST SOT23-6 | Analog Devices Inc | ADG701LBRTZ-REEL7 |

Thermistor drive amplifier 112 is comprised of:

| REF DES | VALUE | Description | MANUFACTURER | MFG P/N |
|---|---|---|---|---|
| R2 | 10K/10K | RES NET 10K/10K OHM ISO 0805 | Susumu | RM2012B-103/103-PBVW10 |
| C14 | 0.1 uF | CAP .10 UF 16 V CERAMIC X7R 0603 | Kemet | C0603C104K4RACTU |
| C15 | 0.1 uF | CAP .10 UF 16 V CERAMIC X7R 0603 | Kemet | C0603C104K4RACTU |
| U9 | LT1722 | IC OPAMP PREC 200 MHZ TSOT-23-5 | Linear Technology | LT1722CS5#TRMPBF |

Thermistor 113 is comprised of GE Thermometrics part number P60AB104L-COEGK. However, it is contemplated that in other embodiments, a person having ordinary skill in the art can choose to use another suitable thermistor.

Trans-impedance Amplifier 114 is comprised of:

| REF DES | VALUE | Description | MANUFACTURER | MFG P/N |
|---|---|---|---|---|
| C39 | 10 pF | CAP CERAMIC 10 PF 50 V NP0 0603 | Kemet | C0603C100J5GACTU |
| R27 | 20K | RES 20.0K OHM 1/10 W .1% 0603 SMD | Susumu | RG1608P-203-B-T5 |

-continued

| REF DES | VALUE | Description | MANUFACTURER | MFG P/N |
|---|---|---|---|---|
| C33 | 1 uF | CAP CERAMIC 1.00 UF 16 V X5R 0603 | Kemet | C0603C105K4PACTU |
| C34 | 1 uF | CAP CERAMIC 1.00 UF 16 V X5R 0603 | Kemet | C0603C105K4PACTU |
| U6 | AD8065 | IC OPAMP FET-IN HP HS SOT23-5 | Analog Devices Inc | AD8065ARTZ-REEL7 |

Control unit 151 is comprised of:

| REF DES | VALUE | Description | MANUFACTURER | MFG P/N |
|---|---|---|---|---|
| J1 | Conn, 20p | CONN FPC 20POS .5 MM SMD R/A ZIF | Molex | 52892-2095-C |
| C37 | 47 uF | CAP TANT 6.3 V 47UF SMD | Nichicon | F950J476MPAAQ2 |
| C38 | 47 uF | CAP TANT 6.3 V 47UF SMD | Nichicon | F950J476MPAAQ2 |

Voltage regulator 105, which provides power to analog-to-digital converter 152, is comprised of:

| REF DES | VALUE | Description | MANUFACTURER | MFG P/N |
|---|---|---|---|---|
| U2 | TPS71525 | IC 2.5 V HI-IN LDO V REG SC70-5 | Texas Instruments | TPS71525DCKR |
| C23 | 1 uF | CAP CERAMIC 1.00 UF 16 V X5R 0603 | Kemet | C0603C105K4PACTU |
| C6 | 0.1 uF | CAP .10 UF 16 V CERAMIC X7R 0603 | Kemet | C0603C104K4RACTU |

In operation, squarewave drive amplifier 124 applies a square wave pulse train having a known frequency, amplitude, and duration to the fluid in cell 125. The square wave pulse train causes a current to flow through the fluid in cell 125. Trans-impedance amplifier 126 measures the amount of current flowing through the fluid in cell 125 and produces an output voltage that is representative of the amount of current flowing through the fluid in cell 125.

Since the voltage of the square wave pulse train applied to the fluid in cell 125 is known (V) and the current flowing through the fluid in cell 125 is known (I), Ohm's law (V=IR) can be used to obtain the resistance of the fluid in cell 125 (R). The resistance value can be used to obtain the conductivity of the fluid in cell 125 since conductivity (G) is the inverse of resistance (G=1/R).

FIG. 3A shows a representation of one period of the square wave pulse train 300 applied by square wave drive amplifier 124 to the fluid in cell 125 in accordance with an embodiment of conductivity meter 100. The square wave pulse train 300 is comprised of a background stage 301, measurement pulse 302, rest stage 303, recovery pulse 304, and base stage 305. In one embodiment, the background stage 301 of the square wave pulse train 300 has an amplitude of zero volts and a duration of 1/(2*drive frequency). The background conductivity of the fluid in cell 125 is measured several times during the background stage 301 by measuring current flowing through the fluid in cell 125 when zero volts is applied to the fluid by square wave drive amplifier 124. The measurement pulse 302 of the square wave pulse train 300 has an amplitude of 2.5 volts and a duration ($t_M$) of 1/(2*drive frequency). The conductivity of the fluid in the cell is measured several times during the measurement pulse 302 by measuring current flowing through the fluid in cell 125 when 2.5 volts is applied to the fluid by square wave drive amplifier 124.

In one embodiment, the rest stage 303 of the square wave pulse train 300 has an amplitude of zero volts and a duration of 50 µs. The rest stage 303 acts to provide separation between the measurement pulse 302 and recovery pulse 304. It is contemplated that in other embodiments, rest stage 303 is not present (has a duration of zero seconds). The recovery pulse 304 of the pulse train 300 has an amplitude of negative 2.5 volts and a has a variable duration. The recovery pulse 304 discharges any residual charge remaining in cell 125 from measurement pulse 302. For the first iteration of the operations taking place within control unit 151, the duration of the recovery pulse ($t_R$) is equal to 1/(2*Drive Frequency). In subsequent iterations, the duration of recovery pulse 304 ($t_R$) is:

$$t_R = RC \ln\left(2 - \exp\left(\frac{-t_M}{RC}\right)\right)$$

where "$t_M$" is the duration of the measurement pulse, and "R" is a parameter estimated or calculated in stages 445, 450, and 455 representing the resistance of the fluid in cell 125, and "C" is a parameter estimated in stages 445 and 450 discussed below. The most recent values for R and C are used to calculate $t_R$.

The base stage 305 has an amplitude of zero volts and has a duration that extends through the remainder of the duty cycle of square wave pulse train 300. About ten (10) data points are captured during the base stage that are used to calculate the temperature of the fluid in cell 125. The temperature of the fluid in cell 125 is measured when multiplexer 153 receives a TEMPERATURE ENABLE signal from control unit 151. Upon receipt of the TEMPERATURE ENABLE signal, multiplexer 153 directs the thermistor circuit voltage output to analog-to-digital converter 152, which passes the digitized thermistor circuit voltage output to control unit 151. The drive frequency and duty cycle, which determine the duration of the background stage 301, measurement pulse 302, recovery pulse 303, and base stage 305, are dictated by Table 1 below. FIG. 3B shows two periods of square wave pulse train 300.

TABLE 1

| Conductivity Range (nS/cm) | TIA Gain[1] | Drive Frequency (Hz)[2] | Measurement Points[3] | Duty Cycle |
|---|---|---|---|---|
| $G_T < 70$ | 3 | $f = 0.625 * G_T + 75$ | 300 | 0.2 |
| $70 \leq G_T \leq 200$ | 3 | $f = 0.625 * G_T + 75$ | 300 | 0.2 |
| $200 < G_T < 2{,}000$ | 2 | $f = 0.4444 * G_T + 111.11$ | $1/(2 * f * 1.7\ \mu s) - 1$ | 0.1 |
| $2{,}000 \leq G_T \leq 35{,}000$ | 1 | $f = 0.0303 * G_T + 939.39$ | $1/(2 * f * 1.7\ \mu s) - 1$ | 0.01 |
| $G_T > 35{,}000$ | 0 | $f = 0.0753 * G_T - 636.13$ | $1/(2 * f * 1.7\ \mu s)$ | 0.01 |

[1]Gains are defined by the setting of gain control circuit 127, gain 3 being the highest gain.
[2]"f" is the drive frequency in Hz and "GT" is the previous raw conductivity value measurement in nS/cm.
[3]Number of points used is defined by the equation, with the maximum number of points being 300. This is the number of data points taken during each of the measurement pulse 302 and background stage 301, which are used to calculate the background conductivity of cell 125 and the conductivity of the fluid in cell 125.

Figure 3C:
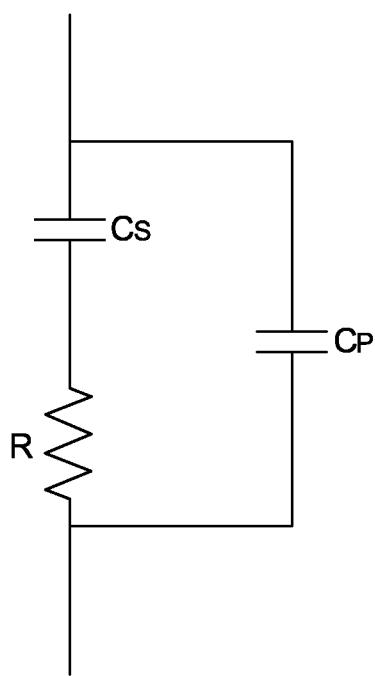
FIG. 3C illustrates the standard model of the conductivity measurement of the fluid in the cell of a conductivity meter according to an embodiment of the present invention.
Figure 3D:
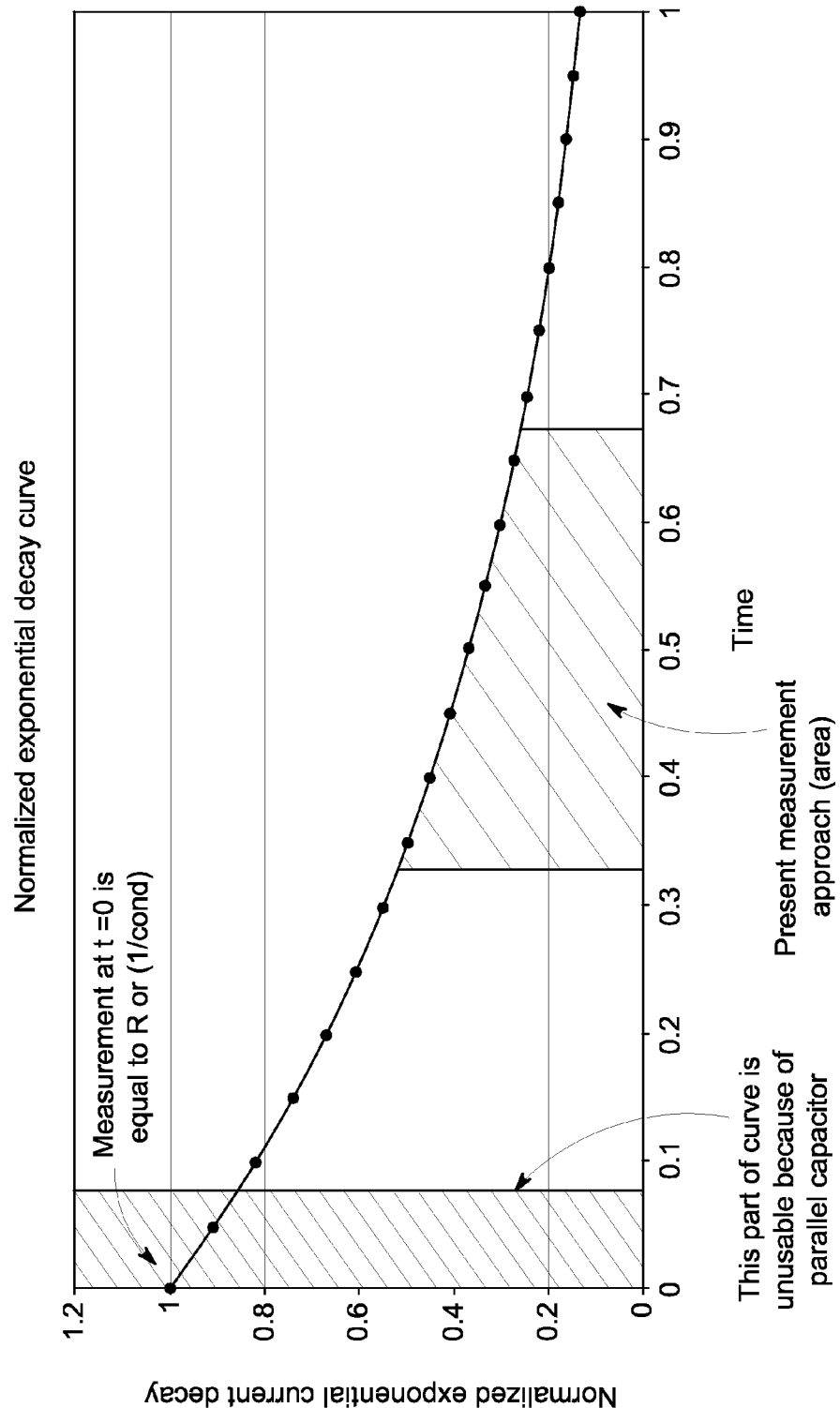
FIG. 3D illustrates the normalized exponential decay curve of the cell of a conductivity meter according to an embodiment of the present invention.

Turning to FIGS. 3C-D, the equivalent circuit of the conductivity measurement of liquid is shown in FIG. 3C. It is a simplified Randles circuit and consists of a resistor (R) in series with a Capacitor (Cs), which represents the double-layer capacity of the electrode/solution interface. That combination has another capacitor (Cp) in parallel. The resistor R is the quantity that is to be measured, as conductivity is 1/R. The measurement is made by applying square wave pulse train 300 (voltage) to the model (cell 125) and measuring the current flowing through the fluid of cell 125. The conductivity of the fluid in cell 125 is directly proportional to the current measured at t=0 in FIG. 3D, when the large current spike caused by Cp at t=0 is ignored (or skipped) as is described below.

The presence of Cp in the circuit causes a large current spike to occur at t=0, which saturates the electronics of cell circuit 120 for a short period of time (shown as the hashed area on the left side of FIG. 3D). Measurements of the current flowing through cell 125 cannot occur, or are unusable, while the electronics of cell circuit 120 are saturated. However, following the current spike at t=0, the exponential decay current curve within cell 125 recovers in an orderly fashion and allows for measurements to be made along the remainder of the curve. Accordingly, the measurement at t=0 is approximated by control unit 151, which applies curve fitting techniques to the measurements taken over the remainder of the curve.

Figure 4A:
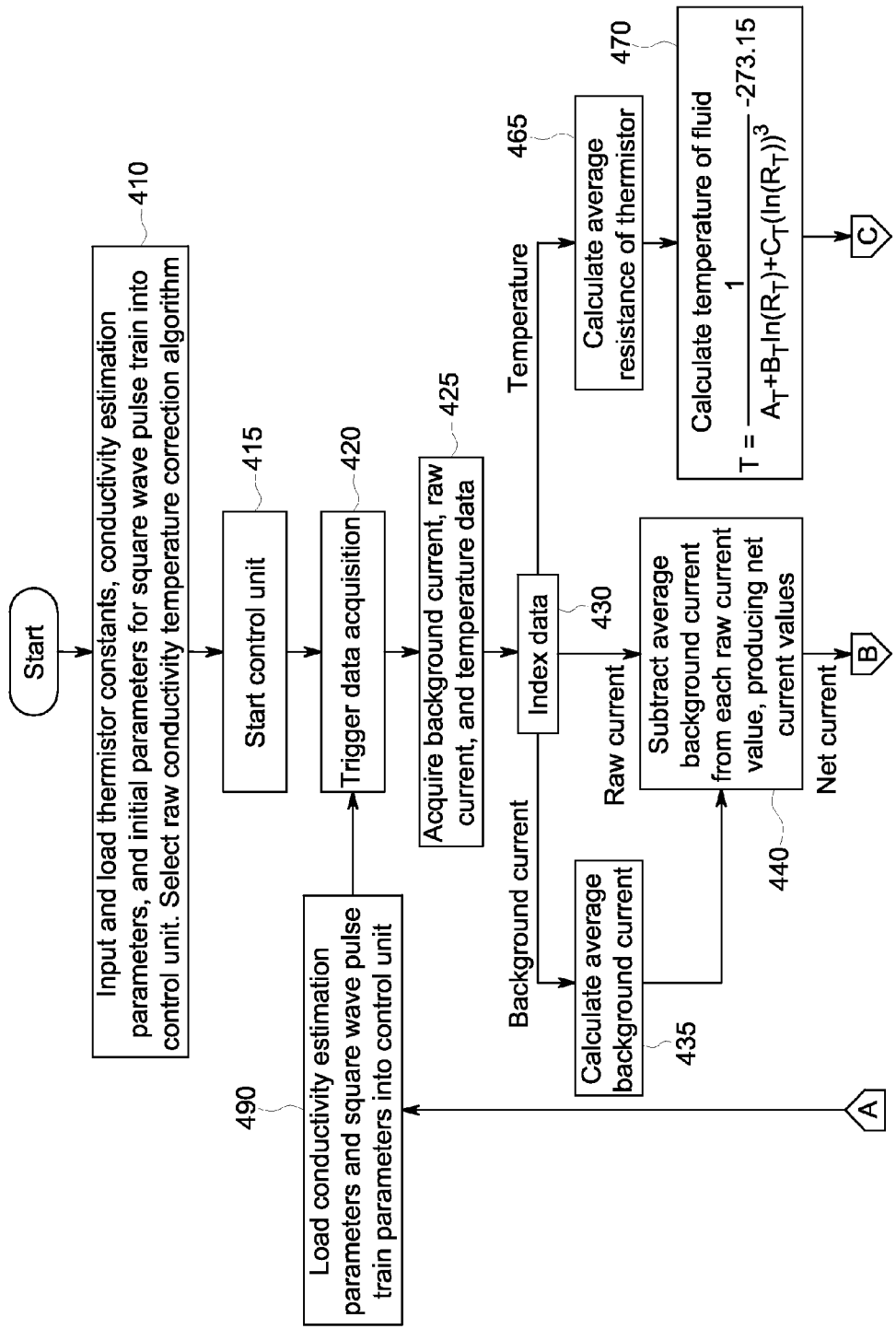
FIGS. 4A-B is a flowchart of the process taking place within the control unit of a conductivity meter according to an embodiment of the present invention.
Figure 4B:
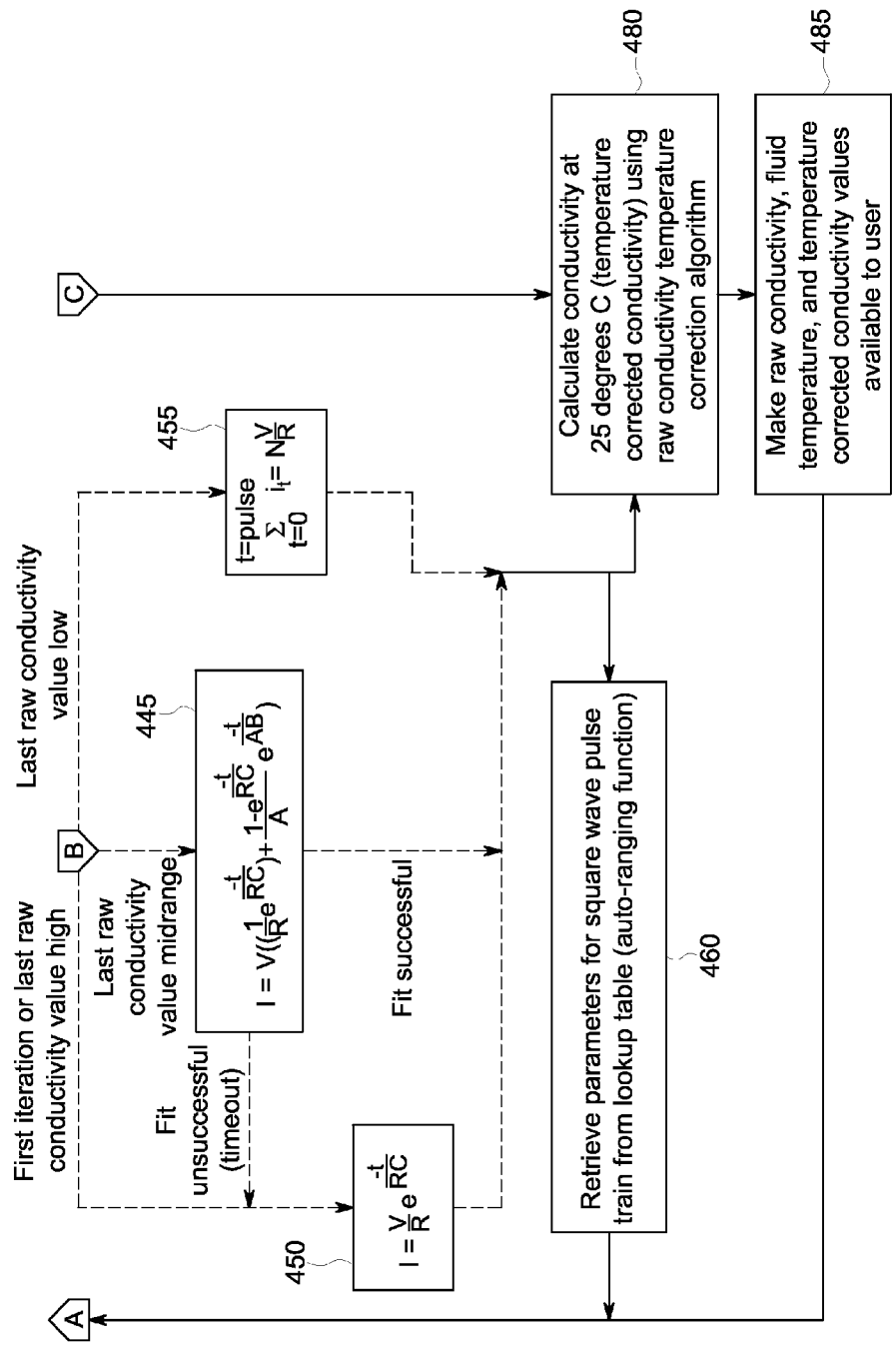

The operations taking place within control unit 151 are detailed in the flowchart of FIGS. 4A-B. The program for performing the operations detailed in the flowchart of FIGS. 4A-B is stored in memory 152 of control unit 151. In stage 410, thermistor constants, conductivity estimation parameters, and initial square wave pulse train generation parameters for the generation of the first square wave pulse train are entered and loaded into control unit 151. The following square wave pulse train generation parameters for the first square wave pulse train are entered and loaded into control unit 151: TIA Gain, Drive Frequency, Measurement Points, and Duty Cycle. For the first iteration of the operations taking place within control unit 151, the duration of the recovery pulse is equal to 1/(2*Drive Frequency). In subsequent iterations, the duration of the recovery pulse is variable and its calculation is discussed below in step 460. The raw conductivity temperature correction algorithm is selected by user. The conductivity estimation parameters: R, A, B, and C are all initialized as having a value of 1.

In stage 415 control unit 151 is started. In stage 420 the data acquisition process is triggered by control unit 151. In stages 425 and 430, the values for background current travelling through cell 125 during background stage 301, values for raw current travelling through cell 125 during the measurement pulse, and temperature data for the fluid in cell 125 is acquired and indexed by control unit 151. The temperature data is comprised of a plurality of values for the amount of current travelling through thermistor 113, which are averaged. The values for current travelling through thermistor 113 are ascertained from the corresponding voltage values produced by trans-impedance amplifier 114.

In stage 465, the average resistance of thermistor 113 is calculated using Ohm's law, V=IR. "V" is the amplitude in volts of the precision voltage applied to thermistor 113 by thermistor drive amplifier 112. "I" is the average amount of current flowing through thermistor 113. Trans-impedance amplifier 114 measures the amount of current flowing through thermistor 113 and outputs a voltage that is representative of the amount of current flowing through thermistor 113. Control unit 151 converts the voltage values obtained from trans-impedance amplifier 114 during the base stage of the pulse train into the corresponding values for current flowing through thermistor 113. Control unit 151 then calculates the average resistance of thermistor "R" is obtained by dividing V by I.

Once the average resistance of thermistor 113 is obtained, the average temperature for thermistor 113 in degrees Celsius can be calculated by control unit 151 using the formula:

$$T = \frac{1}{A_T + B_T \ln(R_T) + C_T (\ln(R_T))^3} - 273.15.$$

In this equation, "T" is the average temperature of thermistor 113 and fluid in cell 125, "$R_T$" is the average resistance of thermistor 113. "$A_T$", "$B_T$", and "$C_T$" are thermistor specific constants available on the data sheet for thermistor 113.

In stages 435 and 440 the values for the background current in cell 125 are averaged, and the average background current value is subtracted from each value of raw current travelling through the fluid of cell 125 during the measurement pulse of the square wave pulse train collected in stage 425, thereby creating net values for the current flowing in cell 125 during the square wave pulse train measurement pulse. Following stage 440, the raw conductivity value for the fluid in cell 125 is calculated using one of the equations in stages 445, 450, or 455.

Control unit 151 will use the equation of stage 450 if the last raw conductivity value measurement was high (e.g. greater than about 1 mS/cm). However, if the last raw conductivity value measurement was low (e.g. less than about 100 nS/cm), control unit 151 will use the equation of stage 455. Control unit 151 will use equation 445 if the last raw conductivity value measurement was midrange, between the high and low conductivity values. It is contemplated that in other embodiments, a person having ordinary skill in the art can choose to use different suitable high and/or low conductivity values.

Further, control unit 151 uses the equation of stage 450 during the first iteration of method 400. Additionally, control unit 151 will calculate the raw conductivity ($G_T$) of the fluid in cell 125 using the equations in stage 450 in the event that the law raw conductivity value measurement was midrange and control unit 151 is unable to fit, within a predetermined length of time, the equation of stage 445 to the net values for the current flowing in cell 125.

When using the double exponent equation of stage 445 shown below, control unit 151 employs a least square method for non-linear equations in order to fit the equation to the net values for the current flowing in cell 125 during the measurement pulse as a function of the elapsed time relative to the rising edge at the beginning of the measurement pulse.

$$I = V\left(\left(\frac{1}{R}e^{\frac{-t}{RC}}\right) + \frac{1 - e^{\frac{-t}{RC}}}{A}e^{\frac{-t}{AB}}\right)$$

A least square method minimizes the sum of the squares of the errors made by subsequent iterative equation. It is contemplated that any suitable least square method for non-linear equations can be used, such as, but not limited to, the Levenberg-Marquardt algorithm. In the equation of stage 445, "R", "C", "A", and "B" are conductivity estimation parameters estimated during the equation fitting process, "t" is the elapsed time relative to the rising edge at the beginning of the measurement pulse in seconds, "V" is the amplitude of the measurement pulse in volts, and "I" is net value of current flowing through cell 125 in amps at a given time t.

Once the equation of stage 445 is fit to the net conductivity data values for the current flowing in cell 125 during the measurement pulse of the square wave pulse train, and parameters R, C, A, and B are estimated, control unit 151 is able to ascertain the raw conductivity ($G_T$) of the fluid in cell 125, which is 1/R. However, if, within a predetermined length of time, control unit 151 is unable to fit the equation of stage 445 to the net values for the current flowing in cell 125 during the square wave pulse train measurement pulse, control unit 151 will calculate the raw conductivity ($G_T$) of the fluid in cell 125 using the equation of stage 450.

In one embodiment, the predetermined length of time for fitting the equation of stage 445 to the net values of current is between about 1 ms-100 ms. However, it is contemplated that in other embodiments, a person having ordinary skill in the art can choose a different suitable predetermined length of time depending upon how quickly the user wants a final conductivity result, as well as the computing power of control unit 151.

When using the single exponent equation of stage 450, control unit 151 employs an ordinary fitting algorithm, which minimizes least squares for linear curves (in log plot), in order to fit the equation to the values for the net current flowing in cell 125 during the square wave pulse train measurement pulse as a function of the elapsed time relative to the rising edge at the beginning of the measurement pulse. Accordingly, a solution to the single exponent equation can be reached using algebra.

$$I = \frac{V}{R}e^{\frac{-t}{RC}}$$

In the equation of stage 450 shown above, "R" and "C" are parameters that are calculated during the curve fitting process, "t" is the elapsed time relative to the rising edge at the beginning of the measurement pulse in seconds, "V" is the amplitude of the measurement pulse in volts, and "I" is the value of net current flowing through cell 125 in amps at a given time "t". Once the equation of stage 445 is solved with respect to R and C, control unit 151 able to ascertain the raw conductivity ($G_T$) of the fluid in cell 125, which is 1/R.

When using the equation of stage 455, control unit 151 calculates an average value for R in order to ascertain the raw conductivity ($G_T$) of the fluid in cell 125, which is 1/R.

$$\sum_{t=0}^{t=pulse} i_t = N\frac{V}{R}$$

In the equation of stage 455 shown above, "R" is the resistance of the fluid in cell 125, "N" is the data set population, "t" is the elapsed time relative to the rising edge at the beginning of the measurement pulse in seconds, "V" is the amplitude of the measurement pulse in volts, and "$i_t$" is value of net current flowing through cell 125 in amps at a given time t.

Once the raw conductivity ($G_T$) of the fluid in cell 125 is ascertained using one of equations in stages 445, 450, or 455, the program progresses to stages 460 and 480.

Since conductivity measurements of a fluid are dependent upon the temperature of the fluid, the industry generally normalize (or temperature correct) conductivity measurements so they appear to have been taken for a fluid having a temperature of 25° C. Accordingly, in stage 480, the raw conductivity temperature correction algorithm, with model chemical compound selected by user in stage 410, is applied to the raw conductivity "$G_T$" to obtain the temperature corrected conductivity value "$G_{T25}$". "$G_T$" is the most recent raw conductivity of the fluid flowing through cell 125 (1/R) calculated in one of stages 445, 450, or 455, "$G_{T25}$" is what the conductivity of the fluid flowing through cell 125 would be if the fluid had a temperature of 25° C. The correction is calculated using the following correction formula:

$$G_{T25} = Gt_{25}(H_2O) + \frac{G_T - Gt(H_2O)}{P},$$

where "$Gt_{25}(H_2O)$" is the conductivity of pure water at 25° C., "$Gt(H_2O)$" is the conductivity of pure water at temperature T (the average temperature of the fluid flowing through cell 125), and P is a polynomial of the form: $P = a_0 + a_1T + a_2T^2 + a_3T^3$, where $a_0$, $a_1$, $a_2$ and $a_3$ are parameters exclusive to the model chemical compound chosen and are derived from The Equivalent Conductance of the Separate Ions table in Smithsonian Physical Tables, Volume 71, by Smithsonian Institution, Frederick Eugene Fowle; page 352, Table 424 (1920), which is incorporated by reference herein and reproduced in relevant part as FIG. 6.

Further, values for "$Gt_{25}(H_2O)$" and "$Gt(H_2O)$" are taken from Table 3, Physical Parameters and Calculated Conductivity and Resistivity, of Light, Truman S., Stuart Licht, Anthony C. Bevilacqua, and Kenneth R. Morashc; *The Fun-*

*damental Conductivity and Resistivity of Water*; Electrochemical and Solid-State Letters. Vol. 8, No. 1 (2005): E16-E19, which is herein incorporated by reference and reproduced in relevant part as FIG. 5. The value of "$Gt_{25}(H_2O)$" is the theoretical conductivity of pure water at 25° C., which is 55.01 nS/cm. The value of "$Gt(H_2O)$" is determined by the temperature of the fluid flowing through cell 125.

Accordingly, if the temperature of the water flowing through cell 125 is 30° C., then the "$Gt(H_2O)$" value will be 70.97 nS/cm. Interpolation is used to ascertain the value of "$Gt(H_2O)$" if the temperature of the water flowing through cell 125 is between two temperature values in FIG. 5. It is contemplated that contents of the table of FIGS. 5 and 6 will be stored in the memory 152 of control unit 151. Control unit 151 will ascertain a value for "$Gt(H_2O)$", using interpolation if necessary, based on the temperature of the water flowing through cell 125.

Accordingly, if the water flowing through cell 125 is 30° C. and the correction is being performed for NaCl, the correction formula would be as follows:

$$G_{T25} = 55.01 + \frac{G_T - 70.97}{P}$$
$$P = -439.14T^3 + 12949T^2 - 13493T + 73214$$

Figure 7:
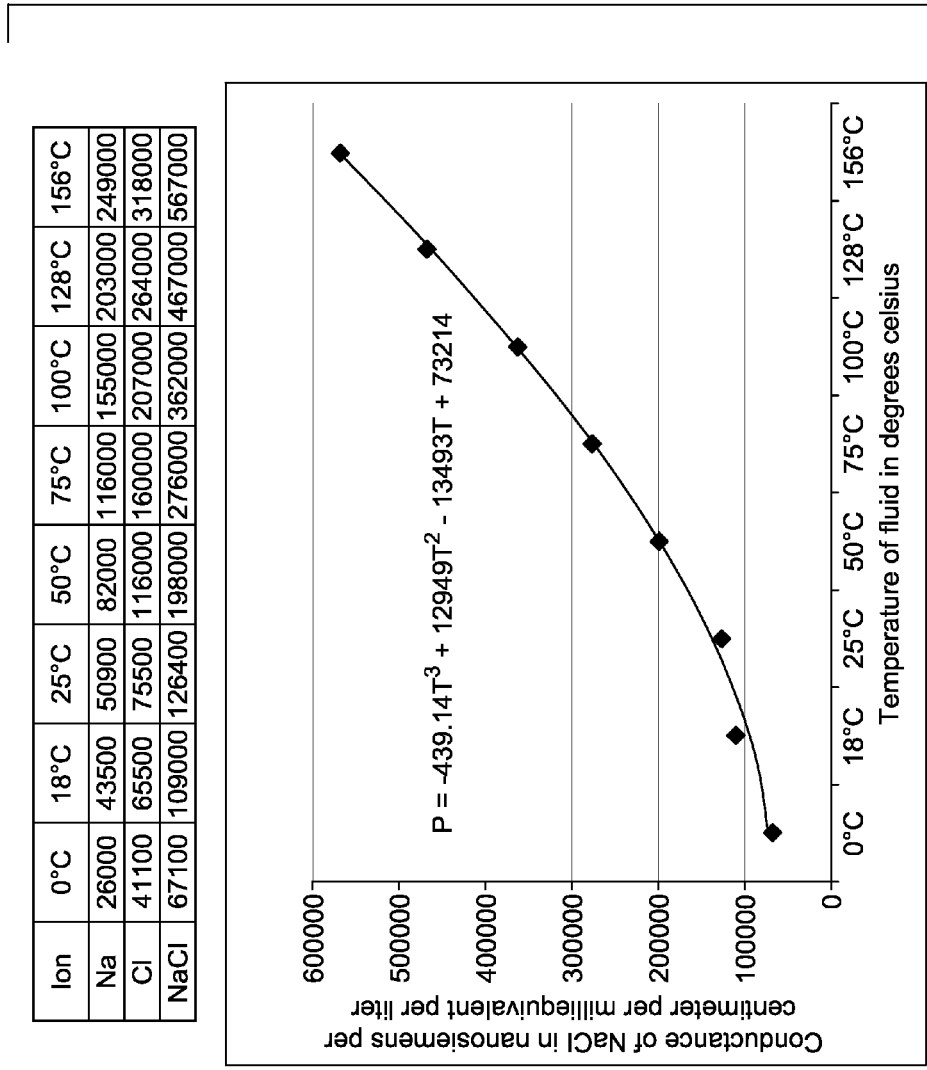
FIG. 7 is a chart plotting datapoints for the equivalent conductance of NaCl vs. temperature and a curve fitted to the datapoints.

As can be seen in FIG. 7, the polynomial, "P" for NaCl is obtained by adding the conductance values for the Na and Cl ions at each given fluid temperature in FIG. 6, plotting the summed conductance values for NaCl vs temperature, and fitting a third degree polynomial through the summed conductance values for NaCl. In FIG. 7, a third degree polynomial is used, however, it is contemplated that a person having ordinary skill in the art may choose to fit a higher or lower degree polynomial to the summed conductance values. It is contemplated that in some embodiments, coefficients for polynomial P for one or more commonly used model chemical compounds are programmed in memory 132 at the factory.

In one embodiment, the temperature correction algorithm is based on model chemical compound NaCl. However, it is contemplated that in other embodiments, a person having ordinary skill in the art can choose to apply a temperature correction algorithm for a different model chemical compound, such as KCl or HCl. Accordingly, it is contemplated that the values for the coefficients for polynomial P corresponding to one or more model chemical compounds will be stored in memory 152. The user will be presented with a listing of the available model chemical compounds and be asked to select a model chemical compound in step 410 for use with the temperature correction algorithm that is applied to the raw conductivity value ($G_T$) in step 480 to produce a temperature corrected conductivity value ($G_{T25}$). Further, it is also contemplated that in some embodiments, a user will be permitted to enter their own coefficient values into control unit 151 and stored in memory 152 for polynomial P in step 410.

In stage 485, the raw conductivity ($G_T$), temperature, and temperature corrected conductivity ($G_{T25}$) values of the fluid in cell 125 are reported to the user via display 160 and stored in control unit 151.

In stages 460, new square wave pulse train generation parameter values for TIA Gain, Drive Frequency, Measurement Points, and Duty Cycle are selected from the lookup table (Table 1 above) based on the most recent raw conductivity ($G_T$) value of the fluid flowing through cell 125 calculated in one of stages 445, 450, or 455. A new value for the duration of recovery pulse ($t_R$) for the next iteration through method 400 is obtained using the following equation, as discussed above:

$$t_R = RC\ln\left(2 - \exp\left(\frac{-t_M}{RC}\right)\right)$$

The new square wave pulse train parameter values are stored in control unit 151 in stage 490. After stage 490 the next data acquisition process is triggered by control unit 151 in stage 420. The new square wave pulse train parameter values stored in control unit 151 determine the properties of the next square wave pulse train in stages 425 and 430. The raw conductivity value ($G_T$) ascertained during the previous iteration of method 400 determines whether the equation of stage 445, 450, or 455 is used by control unit 151 to ascertain the next raw conductivity value using the values for net current flowing in cell 125 acquired during the square wave pulse train measurement pulse in stage 425.

Accordingly, as can be seen, the raw conductivity value ascertained during the previous iteration of method 400 is used to determine the position of gain control circuit switch 130, which determines the cell circuit trans-impedance amplifier feedback resistor value. Further, the raw conductivity value ascertained during the previous iteration of method 400 is also used to determine the new square wave pulse train generation parameter values, and properties of the next square wave pulse train in stages 425 and 430.

While preferred embodiments of the present invention have been described, it should be understood that the present invention is not so limited and modifications may be made without departing from the present invention. The scope of the present invention is defined by the appended claims, and all devices, processes, and methods that come within the meaning of the claims, either literally or by equivalence, are intended to be embraced therein.

What is claimed is:

1. A conductivity meter for measuring the conductivity of a fluid comprising:
   a cell circuit and a control unit circuit;
   said cell circuit comprising a square wave drive amp, a cell, and a trans-impedance amplifier; wherein said fluid flows through said cell;
   wherein said control unit circuit and said square wave drive amp are configured to apply a square wave pulse train having a voltage to the fluid of said cell, thereby inducing a flow of current through said fluid in said cell;
   wherein said cell circuit trans-impedance amplifier and said control unit circuit are configured to obtain a plurality of measurements of current flowing through said fluid in said cell and estimate a raw conductivity of said fluid in said cell using said current flow measurements;
   wherein said control unit circuit estimates the raw conductivity value of said fluid in said cell by fitting said current flow measurements to a double exponent decay function.

2. The conductivity meter of claim 1, wherein said square wave pulse train is comprised of a background stage, a measurement pulse, a recovery pulse, and a base stage.

3. The conductivity meter of claim 2, wherein said square wave pulse train is further comprised of a rest stage.

4. The conductivity meter of claim 2, wherein said measurement pulse has a duration which is determined by a previous raw conductivity value.

5. The conductivity meter of claim 2, wherein said measurement pulse has a duration of 1/(2*drive frequency), wherein said drive frequency is determined by a previous raw conductivity value.

6. The conductivity meter of claim 1, wherein said current flow measurements are values for the net current flowing through said fluid in said cell.

7. The conductivity meter of claim 1 further comprising a thermistor circuit, wherein said thermistor circuit and said control unit circuit are configured to calculate the temperature of said fluid in said cell and apply a temperature correction to said raw conductivity value of said fluid, thereby producing a temperature corrected conductivity value.

8. The conductivity meter of claim 7, wherein said thermistor circuit is comprised of a thermistor switch, thermistor drive, thermistor, and trans-impedance amplifier.

9. The conductivity meter of claim 1, wherein said cell circuit trans-impedance amplifier has a feedback resistor value which is determined by a position of a gain control circuit; wherein said position of said gain control circuit is determined by a previous raw conductivity value.

10. The conductivity meter of claim 1, wherein said cell circuit is further comprised of a polarity switching circuit, wherein said polarity switching circuit is configured to pass voltage to said square wave drive amp and dictate the polarity of said voltage applied to said cell by said square wave drive amp.

11. The conductivity meter of claim 10, wherein said polarity switching circuit is further comprised of a cell switch and a polarity switch.

12. The conductivity meter of claim 10, wherein said cell circuit is further comprised of a rectifier configured to rectify the output of said trans-impedance amplifier.

13. A method for measuring the conductivity of a fluid comprising:
providing a cell circuit having a cell containing a fluid having a conductivity;
applying a square wave pulse train to said cell, thereby causing a current to flow through the fluid in said cell;
obtaining a plurality of measurements of current flowing through said fluid in said cell; and
estimating a raw conductivity value of said fluid by fitting an equation through said current flow measurements, wherein said equation contains the term 1/R, where R equals the resistance of said fluid in said cell, wherein said equation is a double exponent decay function.

14. The method of claim 13, wherein said current flow measurements are values for the net current flowing through said fluid in said cell.

15. The method of claim 13, wherein said square wave pulse train is comprised of a measurement pulse during which said current flow measurements are taken.

16. The method of claim 13, wherein said square wave pulse train is further comprised of a background stage, recovery pulse, and a base stage.

17. The method of claim 16, wherein said square wave pulse train is further comprised of a rest stage.

18. The method of claim 16, further comprising measuring the temperature of said fluid in said cell and applying a temperature correction to said raw conductivity value of said fluid, thereby producing a temperature corrected conductivity value.

19. A system for measuring the conductivity of a fluid comprising:
a control unit; and
memory storing executable code when executed by the control unit performs actions comprising:
applying a square wave pulse train to a cell of a cell circuit containing a fluid having a conductivity, thereby causing a current to flow through the fluid in said cell;
obtaining a plurality of measurements of current flowing through said fluid in said cell; and
estimating a raw conductivity value of said fluid by fitting an equation through said current flow measurements, wherein said equation contains the term 1/R, where R equals the resistance of said fluid in said cell, wherein said equation is a double exponent decay function.

20. The system for measuring the conductivity of a fluid of claim 19, wherein the code when executed by the control unit performs additional actions comprising:
measuring the temperature of said fluid in said cell and applying a temperature correction to said raw conductivity value of said fluid, thereby producing a temperature corrected conductivity value;
wherein said current flow measurements are values for the net current flowing through said fluid in said cell; and
wherein said square wave pulse train is comprised of a measurement pulse during which said current flow measurements are taken, wherein said square wave pulse train is further comprised of a background stage, a rest stage, a recovery pulse, and a base stage.

* * * * *

UNITED STATES PATENT AND TRADEMARK OFFICE
CERTIFICATE OF CORRECTION

PATENT NO.      : 9,116,099 B2  
APPLICATION NO. : 13/728497  
DATED           : August 25, 2015  
INVENTOR(S)     : Vanhoudt et al.

Page 1 of 1

It is certified that error appears in the above-identified patent and that said Letters Patent is hereby corrected as shown below:

Specification

In Columns 13-14, below Table 1, Line 2, delete ""GT"" and insert -- "$G_T$" --, therefor.

Claims

In Column 20, Line 12, in Claim 18, delete "claim 16," and insert -- claim 13, --, therefor.

Signed and Sealed this
Twenty-eighth Day of June, 2016

Michelle K. Lee
*Director of the United States Patent and Trademark Office*